United States Patent [19]

Hinkamp

[11] 4,417,903
[45] Nov. 29, 1983

[54] DIESEL FUEL COMPOSITION

[75] Inventor: James B. Hinkamp, Birmingham, Mich.

[73] Assignee: Ethyl Corporation, Richmond, Va.

[21] Appl. No.: 434,632

[22] Filed: Oct. 15, 1982

[51] Int. Cl.$^3$ .............................................. C10L 1/22
[52] U.S. Cl. ........................................ 44/53; 44/56; 44/57; 260/467
[58] Field of Search ................ 44/53, 56, 57; 260/467

[56] References Cited

U.S. PATENT DOCUMENTS

| 2,905,540 | 9/1959 | Von Schickh et al. | 44/57 |
|---|---|---|---|
| 3,282,983 | 11/1966 | Lachowicz et al. | 260/467 |
| 3,853,944 | 12/1974 | Cummings | 260/466 |
| 4,198,931 | 4/1980 | Malec | 44/56 |
| 4,204,481 | 5/1980 | Malec | 44/56 |
| 4,227,889 | 10/1980 | Perilstein | 44/56 |
| 4,248,182 | 2/1981 | Malec | 44/56 |
| 4,359,324 | 11/1982 | Elsea, Jr. | 44/57 |

OTHER PUBLICATIONS

International Minerals and Chemical Corp. Technical Data Sheet, NP Series TDS, No. 15.

Primary Examiner—Charles F. Warren
Assistant Examiner—Y. Harris Smith
Attorney, Agent, or Firm—Donald L. Johnson; John F. Sieberth; Joseph D. Odenweller

[57] ABSTRACT

The cetane number of diesel fuel is increased by the addition of an aliphatic hydrocarbyl nitro nitrate additive such as 2-methyl-2-nitro-1-propanol nitrate (ester).

7 Claims, No Drawings

DIESEL FUEL COMPOSITION

BACKGROUND

Diesel engines operate by compression ignition. They have compression ratios in the range of 14:1 to 17:1 or higher and for that reason obtain more useful work from a given amount of fuel compared to an Otto cycle engine. Historically, diesel engines have been operated on a petroleum-derived liquid hydrocarbon fuel boiling in the range of about 300°–750° F. Recently, because of dwindling petroleum reserves, alcohol and alcohol-hydrocarbon blends have been studied for use as diesel fuel.

One major factor in diesel fuel quality is cetane number. Cetane number is related to ignition delay after the fuel is injected into the combustion chamber. If ignition delays too long, the amount of fuel in the chamber increases and upon ignition results in a rough running engine and increased smoke. A short ignition delay results in smooth engine operation and decreases smoke. Commercial petroleum diesel fuels generally have a cetane number of about 40–55. Alcohols have a much lower cetane value and require the addition of a cetane improver for successful engine operation.

Through the years, many types of additives have been used to raise the cetane number of diesel fuel. These include peroxides, nitrites, nitrates, nitrosocarbamates, and the like. Alkyl nitrates such as amyl nitrate, hexyl nitrate and mixed octyl nitrates have been used commercially with good results.

Secondary nitrate esters having nitro substitution are disclosed in U.S. Pat. No. 3,282,983. They are made by reaction of an olefin with dinitrogen tetroxide and oxygen followed by reduction of the intermediate peroxynitrate. According to the disclosure it is not possible to make a primary nitrate by this method.

British Pat. Nos. 580,260 and 586,022, as well as British Pat. No. 604,360, U.S. Pat. Nos. 2,453,942 and 2,472,550, are similar and disclose secondary nitrate esters.

SUMMARY

It has now been discovered that the cetane number rating of diesel fuel is greatly increased by the addition of only a very small amount of a primary alkyl nitrate ester which is also substituted with a nitro group. The addition of only 0.05 weight percent 2-methyl-2-nitro-1-propanol nitrate to diesel fuel has given an average increase of 3.77 cetane numbers (range 2.1–5.5). This is much greater than the response given by present commercial cetane improvers.

DESCRIPTION OF PREFERRED EMBODIMENTS

A preferred embodiment of the invention is diesel fuel selected from the group consisting of liquid hydrocarbons of the diesel boiling range, alcohols and mixtures thereof containing a cetane increasing amount of a primary nitrate ester having the structure

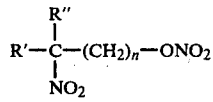

wherein R' is an alkyl group containing 1–20 carbon atoms, R" is selected from the group consisting of hydrogen and alkyl groups containing 1–20 carbon atoms and n is an integer from 1 to 4.

Representative examples of these nitro-substituted primary nitrate esters are:
2-nitro-2-methyl-1-butanol nitrate
2-nitro-2-ethyl-1-octanol nitrate
2-nitro-2-butyl-1-dodecanol nitrate
3-nitro-3-octyl-1-butanol nitrate
3-nitro-3-eicosyl-1-octadecanol nitrate
4-nitro-4-methyl-1-tetracosanol nitrate
2-nitro-1-butanol nitrate
2-nitro-1-docosanol nitrate
2-nitro-2-methyl-1-decanol nitrate and the like.

In a more preferred embodiment, n in the above formula is 1. These compounds include:
2-nitro-2-ethyl-1-propanol nitrate
2-nitro-2-octyl-1-octanol nitrate
2-nitro-2-dodecyl-1-eicosanol nitrate
2-nitro-2-methyl-1-tricosanol nitrate and the like.

In a still more preferred embodiment n is 1 and R" is methyl. These include:
2-nitro-2-methyl-1-octanol nitrate
2-nitro-2-methyl-1-dodecanol nitrate
2-nitro-2-methyl-1-butanol nitrate
2-nitro-2-methyl-1-octadecanol nitrate
2-nitro-2-methyl-1-docosanol nitrate and the like.

The most preferred additive is 2-methyl-2-nitro-1-propanol nitrate.

The additives can be made by nitration of the proper nitro substituted primary alcohol using mixed nitric-sulfuric acid at low temperature (e.g. −15° to 10° C.). The following example shows how to make the nitro-substituted primary nitrate esters.

EXAMPLE

In a reaction vessel was placed 19.1 ml. conc. nitric acid (70 percent). This was stirred and cooled to −27° C. Then 9.2 ml. conc. sulfuric acid (98 percent) was added. Then 17.4 ml. 30 percent oleum was added. Temperature was maintained below −7° C. during these additions. Then 0.2 g. urea was added and the mixture cooled to −17° C. Dropwise addition of 23.8 g. 2-methyl-2-nitro-1-propanol was started. Addition was complete in 32 minutes at −11° to −15° C. The mixture was stirred at −10° C. to −13° C. for 20 minutes and then poured into 150 ml. ice-water mixture. The bottom organic layer was separated and neutralized with sodium bicarbonate and then dried over anhydrous sodium sulfate and filtered giving 26.1 g. of product identified by infrared analysis as 2-methyl-2-nitro-1-propanol nitrate.

Other nitro-substituted primary alkyl nitrates can be made following the above general procedure using different nitro-substituted primary alcohols. For example, 2-methyl-2-nitro-1-octanol will form 2-methyl-2-nitro-1-octanol nitrate.

The amount of cetane improver added depends on the type of fuel being used, the initial cetane value, and the amount of cetane number increase desired. Alcohol fuels such as methanol, ethanol, isopropanol, isobutanol, hexanol, and the like, have very low cetane values and large amounts of cetane improvers are required. A useful range in which to operate is about 5–25 weight percent cetane improver.

Blends of alcohol and petroleum-derived diesel fuel have higher cetane values and require less cetane improver. A useful range is about 0.5–10 weight percent.

Petroleum-derived distillate fuels in the diesel boiling range require only small amounts of cetane improver to achieve a significant increase in cetane number. Such fuels without any cetane improver generally have cetane numbers in the range of about 25–60. Cetane numbers in the range of 25–35 are considered low and those in the range of 50–60 are considered top grade diesel fuels. Diesel fuels in the 35–50 mid-range are most common. An object of the invention is to upgrade the low cetane number fuels at least into the mid-range and to increase the cetane value of the mid-range fuels into the upper portion of the mid-range (e.g. 45–50) or even into the premium range above 50. It has been found that highly beneficial results can be achieved using as little as 0.05 weight percent of the present additive. Accordingly, a useful concentration range in petroleum derived diesel fuel is about 0.01–5 weight percent and more preferably about 0.05–0.5 weight percent.

The cetane increase resulting from the addition of the new additives to diesel fuel was measured using a standard cetane engine. The fuel was a blend of 28 cetane number light cycle oil and 46 cetane number diesel fuel giving a 38.12 cetane number blend. The results are given in the following table in comparison with a commercial cetane improver, isooctyl nitrate.

| Conc. (Wt. %) | 2-Methyl-2-nitro-1-propanol Nitrate | | Isooctyl Nitrate | |
| --- | --- | --- | --- | --- |
| | CN | Gain | CN | Gain |
| None | 38.12 | — | 38.12 | — |
| 0.05 | 41.74 | 3.62 | 39.3 | 1.18 |
| 0.10 | 42.43 | 4.31 | 40.5 | 2.38 |
| 0.15 | 44.70 | 6.58 | 41.8 | 3.68 |

As the above results show, the nitro-substituted primary alkyl nitrate is an outstanding cetane improver, especially at very low concentrations. At 0.15 weight percent, it is 1.79 times as effective as the commercial additive. At 0.10 weight percent, it is 1.81 times as effective. At 0.05 weight percent, it is a surprising 3.07 times as effective as isooctyl nitrate. One other way of making the comparison is that it takes about three times as much (0.15 weight percent) isooctyl nitrate to obtain the same cetane increase as obtained with 2-methyl-2-nitro-1-propanol nitrate (0.05 weight percent).

Other conventional additives may be included in the diesel fuel such as antioxidants, pour point depressants, cold flow improvers, cold filter plugging inhibitors, detergents, rust inhibitors and the like, including other cetane improvers.

I claim:

1. Diesel fuel selected from the group consisting of liquid hydrocarbons of the diesel boiling range, alcohols, and mixtures thereof containing a cetane increasing amount of a primary nitrate ester having the structure

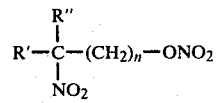

wherein R' is an alkyl group containing 1–20 carbon atoms, R" is selected from the group consisting of hydrogen and alkyl groups containing 1–20 carbon atoms and n is an integer from 1 to 4.

2. A composition of claim 1 wherein said diesel fuel is a liquid hydrocarbon of the diesel boiling range.

3. A composition of claim 2 wherein n is 1.

4. A composition of claim 3 wherein R" is methyl.

5. A composition of claim 4 wherein said nitro-nitrate is 2-methyl-2-nitro-1-propanol nitrate.

6. A composition of claim 5 wherein said nitro-nitrate is 2-alkyl-2-nitro-1-propanol nitrate.

7. A composition of claim 6 wherein said nitro-nitrate is 2-methyl-2-nitro-1-propanol nitrate.

* * * * *